(12) United States Patent
Gallagher et al.

(10) Patent No.: US 11,484,561 B2
(45) Date of Patent: Nov. 1, 2022

(54) MORUS EXTRACTS RICH IN N-ACIDS OF IMINO SUGARS AND OR PIPECOLIC ACIDS

(71) Applicant: Phynova Limited, Long Hanborough (GB)

(72) Inventors: Andrew Gallagher, Long Hanborough (GB); Hongwen Yu, Long Hanborough (GB)

(73) Assignee: Phynova Limited

( * ) Notice: Subject to any disclaimer, the term of this patent is extended or adjusted under 35 U.S.C. 154(b) by 679 days.

(21) Appl. No.: 14/357,008

(22) PCT Filed: Nov. 8, 2012

(86) PCT No.: PCT/GB2012/000833
§ 371 (c)(1),
(2) Date: May 8, 2014

(87) PCT Pub. No.: WO2013/068715
PCT Pub. Date: May 16, 2013

(65) Prior Publication Data
US 2014/0328950 A1    Nov. 6, 2014

(30) Foreign Application Priority Data
Nov. 8, 2011    (GB) .................................. 1119261

(51) Int. Cl.
*A61K 36/605*    (2006.01)
(52) U.S. Cl.
CPC .................... *A61K 36/605* (2013.01)

(58) Field of Classification Search
None
See application file for complete search history.

(56) References Cited

U.S. PATENT DOCUMENTS

| 6,746,695 B1 * | 6/2004 | Martin ................. A61K 36/185 |
| | | 210/656 |
| 2011/0015226 A1 * | 1/2011 | Nash ..................... A61K 31/40 |
| | | 514/315 |

OTHER PUBLICATIONS

Rodrigues-Sanchez S et al., A Derivatization Procedure for the Simultaneous Analysis of Iminosugars and Other Low Molecular Weight Carbohydrates by GC-MS in Mulberry, Food Chemistry, Elsevier Ltd, NL, vol. 126, No. 1, May 1, 2011, pp. 353-359.
Nakagawa K. et al: "Determination of Iminosugars in Mulberry Leaves and Silkworms Using Hydrophilic Interaction Chromatography-Tandem Mass Spectrometry", Analytical Biochemistry, Academic Press, Inc, NY, vol. 404, No. 2. Sep. 15, 2010, pp. 217-222.

* cited by examiner

*Primary Examiner* — Susan Hoffman
(74) *Attorney, Agent, or Firm* — Fishman Stewart PLLC

(57) ABSTRACT

This invention relates to extracts rich in N-acids of imino sugars (as opposed to neutral and basic imino sugars) and/or pipecolic acids obtainable from the plant leaves of mulberry (*Morus*). The extracts have been shown to have enzymatic activities making extracts rich in these compounds, and the compounds isolated from these extracts, to be good candidates for use in the treatment of diseases, particularly, but not exclusively, metabolic disorders, such as, for example, diabetes.

16 Claims, 5 Drawing Sheets

Fig 1

GC-MS 1- Chromatogram of PhynoRadiance Crude Extract

Fig 2

GC-MS 2 Chromatogram of IminoNorm Crude Extract

Fig 3

Mass spectrum 1 (tms) of iminosugar at 9.5 minutes

Fig 4

GC-MS 3 Chromatogram of PhynoRadiance IR120 Retained (iminosugar fraction) 1.38g

Fig 5

GC-MS 4 Chromatogram of IminoNorm IR120 Retained (iminosugar fraction 1) 6.14g

Fig 6a and b

Mass spectra 2 and 3 of two iminosugars not yet identified from IminoNorm

Fig 7a and b

GC-MS 5 Chromatogram of IminoNorm IR120 Retained (iminosugar fraction 2) 23g

Fig 8a b and c

GC-MS Chromatogram of IminoNorm IR120 Retained (iminosugar fraction 3) 25.5g

Fig 9

Mass Spectrum of N-ethanoic acid of DNJ (tms) in PhynoRadiance

Fig 10

Mass Spectrum of DAB-N-ethanoic acid (tms) from PhynoRadiance

Fig 11

Mass Spectrum of N-ethanoic acid of DNJ (tms) in IminoNorm

Fig 12

Mass Spectrum of DAB-N-ethanoic acid (tms) from IminoNorm

Fig 13

Mass Spectrum of N-propanoic acid of DNJ (tms) in IminoNorm

Fig 14

MORUS EXTRACTS RICH IN N-ACIDS OF IMINO SUGARS AND OR PIPECOLIC ACIDS

CROSS-REFERENCE TO RELATED APPLICATIONS

This application is a US National Phase Application of PCT/GB2012/000833, filed on Nov. 8, 2012, which claims priority to GB 1119261.4, filed on Nov. 8, 2011. Both of these applications are hereby incorporated by reference in their entirety.

TECHNICAL FIELD

This invention relates to extracts rich in N-acids of imino sugars (as opposed to neutral and basic imino sugars) and/or pipecolic acids obtainable from the plant leaves of mulberry (*Morus*).

The extracts have been shown to have enzymatic activities making extracts rich in these compounds, and the compounds isolated from these extracts, to be good candidates for use in the treatment of diseases, particularly, but not exclusively, metabolic disorders, such as, for example, diabetes.

Definitions

Imino sugars are a wide spread group of plant and microbial compounds that have the ability to interact with the human glycosidases, other proteins and sugar receptors. In this specification they are considered to be polyhydroxylated secondary and tertiary amines in which the molecules resemble monosaccharide sugars but where the ring oxygen is replaced by nitrogen. There are 5 ring structures fitting this classification that are most common in nature:
  a. pyrrolidine,
  b. piperidine,
  c. pyrrolizidine,
  d. indolizidine, and
  e. nor-tropane.

In nature, the presence of these water soluble secondary plant compounds is largely masked by the presence of other water soluble primary compounds which are present in much larger quantities, such as, for example: common sugars, peptides and amino acids, and further the imino sugar acids (ISA) are masked by the prevailing basic imino sugars such as:
  a. 1 deoxynojirmycin (DNJ),
  b. Fagomine,
  c. 1,4-dideoxy-1,4-imino-D-arabinitol (DAB), and
  d. calystegine B2.

The novel extracts of the invention are rich in the N-acids of the aforementioned imino sugars and include, but are not limited to N-alkyloic acids of the imino sugars such as N-ethanoic, propanoic and butanoic DAB and N-ethanoic, propanoic and butanoic DNJ. They are also rich in pipecolic acids.

By rich is meant that the N-acids of the imino sugars and/or pipecolic acids are present in the extract in an amount, by weight, of greater than 5%, more preferably greater than 10%, and more preferably still greater than 15% (wt/wt).

Preferably a fraction containing both the N-acids of imino sugars and pipecolic acids comprises greater than 10%, through 20%, and 30% to 40%, 50%, 60%, 70%, 80%, 90% or more (wt/wt).

Other components present in an extract will likely include an oligosaccharide component and an amino acid component.

A typical mass balance for an extract will be:
  a. Imino sugar acids 5-25%, typically 15%;
  b. Pipecolic acids 5-35%, typically 20%;
  c. Oligosaccharides 5-25%, typically 15%; and
  d. Amino acids (neutral and acidic) 25-75%, typically 50%.

However, it is possible to reduce the oligosaccharide and amino acid components to increase the relative amounts of the imino sugar acids and pipecolic acids so they comprise the primary components of the extract, and/or isolate individual compounds therefrom.

BACKGROUND

In 1976 Yagi et al, studying the anti-diabetic activity of the mulberry plant isolated DNJ and found it to be a potent inhibitor of the enzyme family of $\alpha$ and $\beta$ glucosidases.

Medicinal chemistry was subsequently employed to the DNJ scaffold to produce N-Hydroxyethyl DNJ (Miglitol) which was successfully developed as an anti-diabetic (Glyset®). However, it's broad glycosidase activity causes side effects.

The present invention is a development of the extract disclosed in WO2011/032502 which describes an extract obtained from the plant leaves of mulberry which inhibits $\alpha$ glucosidase and which can be used to control blood glucose levels.

The specification teaches that the extracts are rich in imino sugars, containing up to 40% by weight. The extract additionally contains up to 70% amino acids.

The described extracts are easily water soluble, pale yellow or nearly white in colour, have a pH of 5.5-6.5 in a 1% water solution, and have maximum absorption peaks at 218 and 263 nm.

The extracts are taught to be useful in controlling blood glucose levels.

The Examples show the compositions to comprise imino sugars in an amount of from 5.2%-39% (w/w) of the extract with the primary imino sugar DNJ present in an amount of from 1.4%-18.6% (w/w) of the total extract, but in all cases the DNJ content comprised at least 19% (w/w) of the imino acid content (measured by it's DNJ, N-methyl DNJ and Fagomine content).

The extracts were prepared by:
  a. Conducting a water or ethanolic extraction;
  b. Conducting a column chromatography with a strong acidic cationic exchange resin and collecting the bound fraction eluted with ammonia;
  c. Subjecting the eluent to column chromatography using a macroporous resin, collecting the eluent; and
  d. Concentrating and drying the extract.

It was observed that the 1050 (inhibiting $\alpha$ glucosidase) in Example 1 (5.8% DNJ, 21% total imino sugars) was 13.6 µg/ml compared to 70 µg/ml for pure DNJ.

Other imino sugars identified in the extract included 1,4-dideoxy-1,4-imino-D-arabinitol (DAB), 2-O $\alpha$-D-galactopyranosyl-DNJ (GAL-DNJ) and calystegine B2.

Furthermore, it is noted that DAB is a glycogen phosphorylase inhibitor.

The resulting fraction typically comprised about from 0.04-1.4% (w/w) of the starting material (*Morus* leaves).

A problem with these and other mulberry extracts, which contain significant amounts of DNJ (typically 5-10% DNJ by weight), is that DNJ is not a selective inhibitor of any one α-glucosidase and, as such, extracts containing significant amounts of DNJ give rise to side effects by inhibiting multiple glucosidases including digestive disaccharidases.

A further problem with seeking to treat metabolic diseases with a single drug entity is that these typically operate via a single mechanism and most metabolic disorders are characterised by multiple effects which would benefit from treatment through multiple mechanisms and not just reducing glucose uptake from the digestive tract.

It is an object of the present invention to develop compositions or isolate compounds which can operate on multiple levels, or offer more specificity, such that they are likely to prove more effective and/or safer in treating diseases, such as metabolic disorders and may be prophylactic or therapeutic.

SUMMARY

In accordance with a first aspect of the present inventions there is provided a purified extract, obtainable from mulberry leaf, characterised in that it is
  a. water soluble;
  b. inhibits α-glucosidase, and
  c. comprises greater than 5% (w/w) N-acids of imino sugars and/or pipecolic acids by weight of the extract.

Preferably the N-acids of imino sugars and/or pipecolic acids comprise at least 10%, through 15%, through 20%, through 30% (w/w) or more of the extract.

Preferably the N-acids of imino sugars comprise C1-C9 alkyloic acids of one or more of DAB, DNJ, Fagomine or calystegine B2. These include the ethanoic, propanoic and butanoic acids.

Preferably the extract further inhibits glycogen phosphorylase. This activity may be in the absence of DAB.

Preferably the extract preferentially and selectively inhibits rice α glucosidase.

A purified extract may further comprise oligosaccharides and amino acids.

In a preferred embodiment a purified extract has a mass balance in which:
  a. Iminosugar acids comprise by weight 5-25% of the extract;
  b. Pipecolic acids comprise by weight 5-35% of the extract;
  c. Oligosaccharides comprise from 5-25% by weight of the extract; and
  d. Amino acids comprise from 25-75% by weight of the extract The amino acids comprise mainly acidic amino acids and the oligosaccharides comprise unusual tri- and larger saccharides with deoxysugars, aryl glycosides and uronic acids.

Most of the non-acidic imino sugars, such as DNJ and DAB are removed such that the imino sugars comprise less than 19% (w/w) DNJ through less than 15% (w/w) through 10% (w/w), through 5% (w/w), through 3% (w/w), through 1% (w/w) DNJ of the imino acid content.

The purified extract is a white semi crystalline or amorphous material and will have been purified by at least a factor of 200 compared with the weight of the starting material and often by more than a factor of 1000.

The purified extract may also act as an inhibitor of one or more of: a naringinase, glucosidase, or mannosidase; a glucuronidase or hexosaminidase; or an α and β galactosidase or I-d-uronidase.

The extract is obtained from
  a. *Morus alba* L.
  b. *Morus alba* var. *multicaulis* L.
  c. *Morus nigra* or
  d. *Morus australis* Poir.

The purified extract is obtained using a strongly acidic cation exchange resin and may further utilise a strongly basic anion exchange resin and/or a weakly basic anion exchange resin in the purification process The selection of an extract in which DNJ is not the primary imino sugar goes against conventional thinking.

The use of extracts rich in N-acids of imino sugars (as opposed to basic imino sugars) and/or pipecolic acids, obtainable from the plant leaves of mulberry (*Morus*), has not previously been suggested.

The extracts of the invention are potent mulberry leaf extracts which are rich in acidic imino sugars and pipecolic acids (and contain very little DNJ or DAB).

In contrast, most commercially available mulberry leaf extracts have an imino sugar content in which DNJ is the most abundant imino sugar, typically accounting for 50% of the mulberry leaf imino sugars (Asano et al. 2001 J. Agric. Food Chem. 49:4208-4213).

Extracts of the present invention are enriched in imino sugar acids (ISAs) and/or pipecolic acids which may be present with or without other constituents such as oligosaccharides and amino acids.

Typical structures of the ISAs present include compounds of the general Formula 1 to 5 below:

Formula 1

R-DAB where R is a C1-C9 straight chained alkanoic group, such as, ethanoic, propionic or butanoic.

Formula 2

R-DNJ where R is a C1-C9 straight chained alkanoic group, such as, ethanoic, propionic or butanoic.

Formula 3

R-Fagomine where R is a C1-C9 straight chained alkanoic group, such as, ethanoic, propionic or butanoic.

R-5-hydroxypipecolic acids

Formula 4 where R is a C1-C9 straight chained alkanoic group, such as, ethanoic, propionic or butanoic, and R-Calystegine B$_2$ Formula 5 where R is a C1-C9 straight chained alkanoic group, such as, ethanoic, propionic or butanoic.

Extracts which are not selective for the imino sugar DNJ, and are instead selective for, and are substantially enriched for ISA content and/or pipecolic acids, are very different from any reported mulberry leaf extracts. More particularly they differ in the following ways:

(1) The extracts of the invention are novel with a completely different chemical profile from that of conventional mulberry leaf extracts. One of the most notable and important chemical features of the extracts of the invention are the provision of a variety of N-substituted imino sugars, which are regarded as a source of promising drug candidates from the imino sugars. Successful examples of substituted imino sugars include N-alkylated imino sugars, which are the only two approved imino sugar based drugs, Miglitol (Glyset)— indicated for type II diabetes, which is a N-2-hydroxyethyl alkylated imino sugar and Miglustat (Zavesca), N-butyl-DNJ, for type I Gaucher's disease and Niemann Pick type C disease, however the present invention teaches of N-alkyloic substitution.

(2) The extracts of the invention have a different and probably favourable biological activity profile from that of conventional mulberry leaf extracts, for example, more specificity in enzyme inhibition to enhance therapeutic efficacy and reduce side effects. The GI side effects caused by DNJ are due to its non-selective inhibition of glucosidases and can be minimised by the reduction in DNJ content. In addition, the N-alkyl substituted ISAs could alter the hydrophilic/hydrophobic property of the active molecules to improve their bioavailability and membrane permeability or binding affinity. Also, the ISAs enriched composition could increase the versatility of the stereo-structures (for example, the chirality) of the active compounds, allowing for chaperon-mediated activity mechanism to be involved in the treatment of relevant diseases, such as lysosomal storage disorders.

(3) The extracts of the invention, owing to their unique features mentioned above, could have an expanded therapeutic spectrum ranging from metabolic syndrome, type I and II diabetes to anti-viral, anti-inflammation or such rare diseases as type I Gaucher's disease.

(4) The extracts of the invention should have a better safety profile. Mulberry leaf is an extremely safe medicinal plant material in its own right and is the sole feed for silkworm and has been used in humans in raw form or as a water decoction for thousands of years in traditional medicine.

(5) The manufacturing process for the extracts of the invention can be easily scaled-up without the use of organic solvents. In conventional phytochemical research, and most current commercial manufacturing process, plant extracts are usually obtained and concentrated by the use of various organic solvents of different polarities, such as ethanol, methanol, ethyl acetate, acetone, dichloromethane, etc. The water-soluble constituents are either left in the plant material or discarded during the purification process. More than often, the process is difficult, if not impossible to repeat in scale-up and solvent residues in the final extract can become an issue.

Thus, to produce extracts according to the invention rich in N-acids of imino sugars and pipecolic acids involves fractionation steps over and above those taught in WO2011/032502. Preferred processes include the use of various ion exchange techniques which include the use of:
  a. A strongly acidic cation exchange resin such as Dowex 50 or IR120;
  b. A strongly basic anion exchange resin such as Dowex 1, Dowex 2, or Amberlite CG400; and
  c. A weakly basic anion exchange resin such as Amberlite IR45.

In accordance with a further aspect of the present invention there is provided a pharmaceutical preparation, dietary supplement or food ingredient comprising the extract of the invention.

In accordance with yet a further aspect of the present invention there is provided the use of a purified extract of the invention for the treatment of metabolic disorders.

The extract may provide one or more of:
  a. Reduced insulin resistance;
  b. Weight loss;
  c. Blood lipid management; and
  d. Beta cell protection.

In a preferred embodiment the extract is used in the treatment of diabetes.

In accordance with yet a further aspect of the present invention there is provided a method of producing a purified extract of the invention comprising the steps of:
  a. Obtaining a water soluble extract from mulberry leaves;
  b. Selecting an imino rich fraction using a strongly acidic cation exchange resin to bind the desired fraction, washing with water, and then eluting the desired fraction with ammonia; and
  c. Selecting for an acidic fraction using one or more of:
    i. A second strongly acidic cation exchange resin;
    ii. A strongly basic anion exchange resin; and
    iii. A weakly basic ion exchange resin.

Preferably in step ci) an un-retained fraction is selected which fraction is further purified using one or more of cii) and ciii).

In accordance with yet a further aspect of the present invention there is provided a method of screening for compounds for use in the treatment of metabolic disorders comprising isolating compounds from an extract of the invention and screening them for enzymatic activity.

BRIEF DESCRIPTION OF THE DRAWINGS

The invention is further described, by way of example only, with reference to the following Examples and the accompanying drawings relating to Examples 4 and 5, in which.

DETAILED DESCRIPTION

The Examples given below provide exemplification of how the claimed extracts and isolated compounds of the invention may be produced and used to treat the conditions claimed, and are provided by way of example only.

The starting point for a consideration of the claimed invention is the extract disclosed in WO2011/032502.

Contrary to conventional reasoning the Applicant, noting that the a glycosidase activity of the extract was greater than that of pure DNJ, decided to remove the DNJ and look at the activity of different sub-fractions. These experiments identified a fraction rich in the N-acids of imino sugars and pipecolic acids that exhibited good activity and details of the experiments giving rise to this finding are set out below:

Example 1

Starting Extract
Dried extract of *Morus alba* leaves Batch ML091210
Method

The sample was dissolved in water and fractionated by a strongly acidic cation exchange (IR120 H$^+$ form resin in column of 2×30 cm) chromatography to give
  i. an un-retained sample displaced by water (expected to contain mainly sugars, flavonoids etc.);
  ii. a bound fraction displaced by 2M pyridine (usually removes remaining sugars, phenolics and neutral and acidic amino acids); and
  iii. a bound fraction displaced by 2M ammonia solution (expected to contain any alkaloids [iminosugars] and basic amino acids).

Some DNJ was detected in the un-retained material (perhaps due to overloading or pH of the sample) and so this was passed through a second IR120 column (same dimensions) to give a new un-retained sample and a second ammonia fraction. The second un-retained sample contained no DNJ.

The fractions are set out in Table 1 below.

| Sample | Weight in g |
| --- | --- |
| a) IR120 Un-retained fraction | 5.026 |
| b) Pyridine displaced fraction | 1.743 |
| c) 1$^{st}$ Ammonia displaced fraction | 1.592 |
| d) 2$^{nd}$ ammonia displaced fraction | 0.469 |

The fractions were freeze dried and weighed. Aliquots were analysed by GC-MS and by 500 MHz NMR spectroscopy (in D$_2$O). DNJ quantity was determined both by GC-MS and NMR data.

GC-MS

All samples were freeze dried before derivatisation. Trimethylsilyl (TMS) derivatives were prepared using a mixture of hexamethyldisilazane and trimethylchlorosilane in pyridine (Pierce Tri-Sir silylation reagent, HMDS:TMCS:pyridine in a ratio of 2:1:10). Samples were heated at 60° C. for 15 minutes and then left at room temperature for at least 60 min. Insoluble reaction products were sedimented by centrifugation, and the supernatant was transferred to fresh vials using a syringe.

Analysis was carried out by GC-MS using a Perkin Elmer Autosystem XL gas chromatograph with a high polarity fused-silica column (Varian 'Factor Four' VF-5 ms column, 25 m×0.25 mm i.d., 0.25 µm phase thickness). The carrier gas (helium) flow rate was 1 ml min-1. Trimethylsilyl-(TMS) derivatives were separated using a temperature programme that started at 160° C. for 5 min, followed by a linear increase to 300° C. at a rate of 10° C. min-1. The temperature was held at 300° C. for an additional 10 min; the total analysis time was 29 min. Electron impact mass spectrometry of the column eluant was carried out using a Perkin Elmer TurboMass Gold mass spectrometer, with a quadrupole ion filter system, which was run at 250° C. constantly during analysis. The detector mass range was set to 100 to 650 amu. The temperature of the transfer line (GC to MS) was held at 250° C. Samples were injected onto the column via a split vent (split ratio 50:1) through a fused silica narrow bore injection liner packed with deactivated quartz wool; the injection port temperature was maintained at 200° C. The injection volume was 1 µl. System control, data collection and mass spectral analysis was carried out using Perkin Elmer TurboMass software (TurboMass v. 4.4). Quantification of DNJ was carried out by comparing peak areas in the samples (1 mg of each sample in a vial) with a calibration curve using pure DNJ (0.05-0.33 mg per vial). Quantification was confirmed by estimation of DNJ in the samples using NMR data.

Glycosidase Assays

The assays used p-nitrophenyl-substrates and commercial enzymes purchased from Sigma-Aldrich. Enzymes were assayed at 27° C. in 0.1M citric acid/0.2M disodium hydrogen phosphate buffers at the optimum pH for the enzyme. The incubation mixture consisted of 10 µl enzyme solution, 10 µl of 10 mg/ml aqueous solution of extract and 50 µl of the appropriate 5 mM p-nitrophenyl substrate made up in buffer at the optimum pH for the enzyme. The reactions were stopped by addition of 70 µl 0.4M glycine (pH 10.4) during the exponential phase of the reaction, which had been determined at the beginning using uninhibited assays in which water replaced mulberry fractions. Final absorbances were read at 405 nm using a Versamax microplate reader (Molecular Devices). Assays were carried out in triplicate, and the values given are means of the three replicates per assay. Results are expressed as % inhibition.

Results

The GC-MS chromatograms (not shown) of the IR120 fractions were all dominated by DNJ.

The un-retained material was mainly sugars and contained no DNJ or other imino sugars after the second IR120 column.

Other imino sugars and imino sugar acids (hydroxylated non-protein imino acids) were also detected by their characteristic mass spectra.

The DNJ levels in the three retained fractions b), c) and d)—Table 1 was determined and is shown in Table 2:

Quantification of DNJ in Samples by GC-MS

TABLE 2

|  | GC-MS Peak Area | DNJ mg/mg of sample | Total wt of sample in mg | DNJ in IR120 fraction (mg) |
|---|---|---|---|---|
| b) Pyridine | 92 | 0.068 | 1743 | 118.5 |
| c) Ammonia 1st IR120 column | 313 | 0.2 | 1592 | 318.4 |
| d) Ammonia 2nd IR120 column | 61 | 0.0461 | 469 | 21.6 |
| Total DNJ |  |  |  | 458.5 mg in 10 g |

Assuming the same detector response for fagomine, DAB, pipecolic acids (combined) and the 13.35 minute imino sugar, the amount of these compounds in the 10 g are estimated as:

| a. Fagomine | 51 mg |
| b. DAB | 7.5 mg |
| c. Pipecolic acids (combined) | 167 mg |
| d. 13.35 minute iminosugar | 7 mg |

NMR analysis (not shown) showed the material not retained on IR120 to be mainly sugars; this fraction was approximately 50% of the 10 g sample by weight after cation exchange.

The major nitrogen-containing components with DNJ were determined to be amino acids (precise identification not available but phenylalanine and proline were tentatively identified by GC-MS)

Glycosidase Assays

In house glycosidase assay results are shown in Table 3.

The inhibition of α- and β-glucosidases for the IR120 retained fractions was expected given the presence of significant amounts of DNJ.

The inhibition of other glycosidases such as glucuronidase and hexosaminidases could not be attributed to DNJ, DAB or fagomine. It was probable that the major components identified as pipecolic acids were responsible for these other glycosidase inhibitions.

Elevated serum levels of glucuronidase and hexosaminidase activities are observed in many diseases including diabetes.

TABLE 3

Glycosidase Results for Fractions

| mulberry fraction | α-D-glu Yeast | α-D-glu Bacillus | α-D-glu rice | β-D-glu almond | α-D-gal green coffee bean | β-D-gal bovine | α-L-fuc bovine | α-D-man Jack bean |
|---|---|---|---|---|---|---|---|---|
| IR120 unb | 49 | 68 | 97 | 0 | −17 | 32 | −15 | −10 |
| ammonia 2 | 85 | 97 | 100 | 66 | 60 | 34 | 0 | −12 |
| ammonia 1 | 98 | 100 | 100 | 89 | 94 | 67 | 0 | 25 |
| pyr | 85 | 99 | 100 | 83 | 77 | 37 | 0 | 0 |
| DNJ | weak | potent | potent | moderate | weak | NI | NI | weak |

| mulberry fraction | β-D-man Cellulomonas | naringinase Penecillium | N-acetyl-β-D-gluc (Bovine kidney) | N-acetyl-β-D-gluc (Jack bean) | amyloglucosidase (A. niger) | β-glucuronidase (bovine liver) |
|---|---|---|---|---|---|---|
| IR120 unb | −6 | −7 | 14 | −13 | 8 | 6 |
| ammonia 2 | 0 | 6 | 22 | 31 | 71 | 24 |
| ammonia 1 | 8 | 32 | 39 | 92 | 96 | 0 |
| pyr | 0 | 16 | 22 | 84 | 82 | 6 |
| DNJ | NI | NI | NI | NI | NI | NI |

Results are expressed as % inhibition at top concentration of 10 mg/ml (prior to dilution in the assay).

NI = no inhibition.

A negative value suggests promotion or stabilisation of the enzyme.

The typical DNJ inhibitory activity is shown for reference.

DISCUSSION

The IR120 retained fractions all contain DNJ but the analysis and glycosidase results show a wider range of glycosidase inhibitors to be present.

The IR120 un-retained material also showed some glycosidase inhibitions that is surprising but this is likely attributed to the sugars which are dominant in this fraction and can interfere with glycosidase assays.

DNJ, DAB and fagomine are all glucosidase inhibitors and it is interesting that the IR120 retained fractions give good inhibitions of glycosidases not affected by DNJ.

Some of these enzyme activities such as hexosaminidase and glucuronidase are known to be elevated in serum or urine in various diseases including diabetes.

In the subsequent Examples these fractions were further fractionated to more conclusively identify the more major compounds responsible for the activities.

The pipecolic acids compounds are particularly interesting.

Example 2

The Extract of Example 1 was fractionated into four fractions using cation exchange chromatography (IR120 H+ form).

The un-retained fraction contained sugars with iminosugars displaced with pyridine and then ammonia.

Some DNJ was found in each retained fraction but most was in the first ammonia fraction. Other imino sugars were also detected including tentatively fagomine, DAB, some hydroxylated imino acids and other potentially novel iminosugars.

Table 4 below shows the enzyme inhibitions noted for the fractions in Example 1.

| Sample | Weight in g | Glycosidases inhibited | DNJ mg/mg of sample | Total weight of fraction in g |
|---|---|---|---|---|
| IR120 unretained fraction | 5.026 | Gp 56% α-glucosidases β-glucuronidase (weak) | 0 | 5.026 |
| Pyridine fraction | 1.743 | Gp 84% α-glucosidases β-glucosidase α-galactosidase β-galactosidase Naringinase Hexosaminidase β-glucuronidase (weak) | 0.068 | 1.743 |
| 1$^{st}$ ammonia fraction | 1.592 | Gp 97% α-glucosidases β-glucosidase α-galactosidase β-galactosidase Naringinase Hexosaminidase α-mannosidase | 0.0461 | 1.592 |
| 2$^{nd}$ ammonia fraction | 0.469 | Gp 84% α-glucosidases β-glucosidase α-galactosidase β-galactosidase Naringinase Hexosaminidase β-glucuronidase | 0.0461 | 0.469 |

In Example 2 the aim was to:
a. Further resolve the components in all four fractions;
b. Analyse compounds by GC-MS and 500 MHz NMR to identify as many components as possible; and
c. Conduct glycosidase assays on purified compounds to further distinguish the inhibitions given by the different components.

Analysis

This Example primarily involved further fractionation of the 10 g of *Morus alba* leaf extract used in Example 1

GC-MS

This was conducted as per Example 1.

NMR

This was conducted as per Example 1.

Glycosidase Assays

This was conducted as per Example 1.

Methods of Purification a) Sugar Components (IR120 Un-retained)

The IR120 un-retained fraction from Example 1 was shown by GC-MS to contain primarily sugars but gave rather surprising activity in the glycosidase assays (including glycogen phosphorylase). This sample was therefore further fractionated to separate the common sugars from more unusual components (probably giving the activity) and to remove some brown colour (probably phenolics).

The 5 g was dissolved in a minimum volume of distilled water and applied to a column (2×10 cm) of Amberlite CG400 anion exchange resin in the OH— form.

Eleven 2 ml water fractions were collected before removing retained material with 1M HOAc. Samples were dried and analysed by GC-MS, NMR and on the basis of the analysis some were provided for glycosidase and glycogen phosphorylase assays. Some brown material was bound permanently to the resin.

The sugar fractions obtained were colourless or slightly yellow. Some were recombined for further separation later. The fractions are shown in Table 5 below.

| Fraction from CG400 | Weight in mg |
|---|---|
| 1-10 | 765 |
| 11 | 364 |
| HOAc 1 | 100 |
| HOAc 2 | 1,2697 |

The total weight of sugars, therefore, appears to be in the region of 3.728 g in the 10 g sample although it is possible that some inorganic material is not being detected by GC or NMR.

b) Pyridine and Ammonia Fractions

The IR120 pyridine and ammonia fractions 1 and 2 were further fractionated to reduce the DNJ present with other components to allow their structural elucidation by NMR.

To achieve this a series of columns were run using:
a. Anion exchange chromatography (Amberlite CG400 in the OH⁻ and Ac⁻ forms) and
b. Cation exchange chromatography using a weakly acidic resin (Amberlite CG50 in the ammonium form).

Results a) Sugar Fractionation

The CG400 fractionation of sugars (IR120 un-retained material from Example 1) showed sugar alcohols in earlier fractions. Some common monosaccharides (furanose and pyranose) occurred throughout the fractions. Disaccharides increased and then further monosaccharides showed in the main acetic acid fraction (some perhaps due to acid hydrolysis). Interestingly all fractions tested gave both glycosidase and glycogen phosphorylase inhibition. Several unusual components were detected.

b) Iminosugar Fractionation (from IR120 Pyridine and Ammonia Fractions)

From the IR120 bound fractions obtained in Example 1 several components were partially purified allowing further characterization.

A compound with a retention time 10.37 min gave good matches by GC-MS with structures derived from DAB.

The compounds with retention times of 12.91 and 13.31 minutes gave good matches to piperidine N-acid type compounds which might be derived from DNJ.

A component with GC retention time of 19.36 minutes was purified—3.3 mg. This component gave mass spectral data consistent with a glycoside although it is unusual to have glycosides bound to IR120 resin.

Attempts were made to further purify the fagomine and DAB type compounds. Some of these were eventually obtained in a single fraction of 2.0 mg.

Pipecolic acids were identified in fraction JH0806/101/23.

All five fractions were submitted for enzyme assays in addition to sugar fractions and trigonelline (observed in NMR spectra Formula 6) and 6-hydroxytrigonelline (Formula 7) (possibly observed in NMR spectra but very minor component).

Trigoneline

Formula 6

6-hydroxytrigonelline

Formula 7

Glycosidase Assays on Compounds and Fractions

The assay results for the fractions are given in Table 6

TABLE 6

| compound | PQ code | α-D-glucosidase Yeast | α-D-glucosidase *Bacillus* | α-D-glucosidase rice | β-D-glucosidase almond | α-D-galactosidase coffee bean | β-D-galactosidase bovine | α-L-fucosidase bovine |
|---|---|---|---|---|---|---|---|---|
| 19.4 min disacch. comp | JH806/78/45 | 8 | 53 | 90 | 97 | 9 | 50 | −6 |
| *Calliandra* pipecolic acid | JH806/87/4 | 0 | 34 | 54 | 0 | −7 | 0 | 0 |
| DAB N-acid tentative | JH806/93/4 | 23 | 58 | 97 | 8 | 0 | 0 | 0 |
| pipecalic acids | JH806/101/23 | 0 | 33 | 59 | 0 | −6 | 0 | 0 |
| DAB and fagomine | JH806/106/8 | 98 | 96 | 56 | 25 | −11 | 21 | ND |

| compound | α-D-mannosidase Jack bean | β-D-mannosidase *Cellulomonas fimi* | naringinase *P. decumbens* | N-acetyl-β-D-gluc Bovine kidney | β-N-acetyl-β-D-gluc *A. oryzae* | β-glucuronidase bovine liver |
|---|---|---|---|---|---|---|
| 19.4 min disacch. comp | −18 | −12 | 0 | 15 | 0 | 0 |
| *Calliandra* pipecolic acid | 0 | −6 | 0 | 0 | 0 | −6 |
| DAB N-acid tentative | −6 | 0 | 0 | 8 | 0 | 0 |
| pipecalic acids | 0 | 0 | 0 | 0 | −6 | −6 |
| DAB and fagomine | 0 | 15 | 0 | −7 | −6 | 0 |

| type | number | α-D-glucosidase Yeast | α-D-glucosidase *Bacillus* | α-D-glucosidase rice | β-D-glucosidase almond | α-D-galactosidase coffee beans | β-D-galactosidase bovine | α-D-mannosidase jack bean |
|---|---|---|---|---|---|---|---|---|
| compound | 900439 | 0 | 0 | 0 | 0 | −6 | 0 | 0 |
| commercial | trigonellin HCl | 0 | −12 | 0 | 0 | 0 | 0 | 0 |
| 6OH trig | Jh808/6/13 | 0 | −36 | 0 | 0 | −16 | 8 | 0 |
| sugar | JH808/4/35 | 0 | −9 | 0 | 0 | 0 | 0 | 5.7 |
| RN sugars | 5* | 7 | 41 | 92 | 0 | −9 | 0 | ND |
| RN sugars | 10* | 75 | 81 | 97 | 6 | 0 | 6 | ND |
| RN sugars | 11* | 25 | 26 | 82 | 0 | −8 | 0 | ND |
| RN sugars | HOAc* | 0 | −14 | 57 | 0 | −15 | 16 | ND |

| type | number | β-D-mannosidase *C. fimi* | naringinase *Penecillium* | N-acetyl-β-D-gluc Bovine kidney | N-acetyl-β-D-gluc Jack bean | amyloglucosidase *A. niger* | β-glucuronidase bovine liver |
|---|---|---|---|---|---|---|---|
| compound | 900439 | 0 | −6 | 9 | 8 | 0 | 0 |
| commercial | trigonellin HCl | 0 | 0 | −8 | 0 | 0 | 0 |
| 6OH trig | Jh808/6/13 | 0 | 0 | 12 | −11 | 0 | 0 |

TABLE 6-continued

| | | | | | | | |
|---|---|---|---|---|---|---|---|
| sugar | JH808/4/35 | 0 | 0 | 14 | 11 | 8 | 0 |
| RN sugars | 5* | ND | −7 | 0 | 0 | 0 | −7 |
| RN sugars | 10* | ND | 0 | 9 | 7 | 24 | 0 |
| RN sugars | 11* | ND | 0 | 0 | 0 | 6 | 0 |
| RN sugars | HOAc* | ND | −6 | 0 | 0 | 0 | 0 |

*run at 2 mg/ml.
ND = not determined

Glycogen Phosphorylase Assay Results
These assay results are given in Table 7 below.

| Compound | GP Inhibition (%) |
|---|---|
| Trigonelline | 6.9% at 400 µM |
| JH0808/6/13 6-hydroxytrigonelline | 11.9% at 400 µM |
| JH0808/4/35 disaccharide | 1.7% at 400 µg/mL |
| 900439 (structure) | 0% at 400 µM |
| Sugars 5 | 63.5% at 1 mg/m |
| Sugars 11 | 55.3% at 1 mg/ml |
| Sugars HOAc | 48.9% at 1 mg/ml |

Discussion and Conclusion

It has been possible to identify imino-sugars including some novel natural compounds tentatively identified as N-acids of DAB and DNJ.

The sugar fraction of the sample also shows both glycosidase and glycogen phosphorylase inhibition.

Sugars such as glucose and sucrose do not inhibit glycogen phosphorlyase or glycosidases.

Some unusual components were identified as present in the sugar fractions by GC-MS and it is presumed that these are responsible for the inhibition of the glycosidases and glycogen phosphorylase. The sugar fractions are a high proportion of the unfractionated extract and so may contribute significantly to the activity of the sample.

Although DAB is reported to give glycogen phosphorylase inhibition, the unfractionated extract clearly has several imino-sugar components which give this inhibition.

The pipecolic acids and trigonelline identified in Extracts were not greatly inhibitory to the glycogen phosphorylase. DNJ and fagomine do not inhibit this enzyme. It may well be that the N-acids of DAB and DNJ are the active components After removing the DNJ, DAB and fagomine, many components in the extract also inhibited the glucosidases.

Example 3

The analysis conducted on the fractions described in Example 2 provided further information on the imino-sugars and sugars of the sample.

The sugar fraction comprised almost half of the sample and showed potent activity against various glycosidases and glycogen phosphorylase.

Sugars such as sucrose, trehalose and glucose do not inhibit these enzymes significantly.

In this Example an attempt was made to characterise the active components of the sugar fraction and look further at its activity.

In this regard it was fractionated further using a series of ion exchange columns.

Method

The IR120 un-retained fraction from Example 1 was submitted to chromatography on an anion exchange resin CG400 (OH⁻ form) to yield water fractions (1-11) and two acetic acid fractions (Table 5—Example 2). These were still further fractionated in this Example and the activity of the fractions was further investigated.

Analysis
GC-MS
This was as per Example 1.
NMR
This was as per Example 1.
Glycosidase Assays
This was as per Example 1.
Methods of Purification The further fractionation of the sugar samples involved use of a strongly basic anion exchange resin CG400 used in the OH— form and also in the acetate form.

Fractions were collected in water and freeze dried. Retained material was removed using 1M acetic acid and these fractions were evaporated nearly to dryness by rotary evaporation and then freeze dried.

Results

To further purify the sugar samples and to remove any possible inorganic material all samples were re-chromatographed through CG400 OH— form. Sugar fractions 1-11 were combined into sample 1-11 and the two acetic acid samples were also recombined.

Both samples were loaded on a CG400 OH— 2×20 cm column and water fractions collected before a final wash with 1M HOAc to remove retained material.

The fraction weights are shown in Table 8 below.

| Fraction number CG400 OH- | Weights of fractions from combined sample 1-11 | | Weights of fractions from acid fraction | Notes |
|---|---|---|---|---|
| 1 | 0 | | 0.7 mg | Yellowish |
| 2 | 55.3 mg | White semi-crys | 1.8 mg | White amorphous |
| 3 | 82.3 mg | White semi-crys A | 0.9 mg | White amorphous | 3-7 combined as E 2.1 mg |
| 4 | 86 mg | White semi-crys | 0.9 mg | White amorphous |
| 5 | 63.8 mg | White semi-crys | 1 mg | White amorphous |

-continued

| Fraction number CG400 OH- | Weights of fractions from combined sample 1-11 | | Weights of fractions from acid fraction | Notes |
|---|---|---|---|---|
| 6 | 53.5 mg | White semi-crys | 0.8 mg | White amorphous |
| 7 | 81.1 mg | White semi-crys B | 0.9 mg | White amorphous |
| 8 | 53.3 mg | White semi-crys | 0.9 mg | White amorphous 8-14 combined as F 11.7 mg |
| 9 | 34 mg | White semi-crys | 1.1 mg | White amorphous |
| 10 | 7.1 mg | Clear syrupy | 2.1 mg | White amorphous |
| 11 | 1.4 mg | Clear syrup | 3.8 mg | White amorphous |
| 12 | 1 mg | Clear syrup | 3 mg | White amorphous |
| 13 | 0.1 mg | Clear syrup | 2.8 mg | White amorphous |
| 14 | 1.4 mg | Clear syrup | 1 mg | White amorphous |
| 15 | 1.2 mg | Clear syrup | — | — |
| 16 | 1.2 mg | Clear syrup | — | — |
| 17 | 0.8 mg | Clear syrup | — | — |
| HOAc wash | 545 mg C HS119 | clear light yellow syrup | 989 mg D HS120 | clear light yellow syrup The retained material was further fractionated on CG400 acetate form resin |

Surprisingly the sample 1-11 that was un-retained on the first CG400 OH— column now gave a considerable weight that was retained. This suggests a pH effect or possible overloading of the first column.

The un-retained fractions of sample 1-11 were white semi-crystalline material as before.

The acid sample gave most weight in the retained fraction as expected but small amounts of material were un-retained and sample 3-7 had most glycosidase inhibition activity.

The early 1-11 fractions had white solid semi-crystalline material that gave no GC peaks suggesting sugars that were larger than disaccharides.

Later fractions showed some sugar alcohols but low amounts.

Samples coded A-F in Table 8 were submitted for NMR analysis.

A, B, E and F were also submitted for glycosidase assays the results of which are tabulated in Table 9 below.

TABLE 9

Activity (% inhibition) of Sugar Fractions on Glycosidases

| sample | α-D-glucosidase (Yeast) | α-D-glucosidase (Bacillus) | α-D-glucosidase (rice) | β-D-glucosidase (almond) | α-D-galactosidase (green coffe bean) | β-D-galactosidase (bovine) |
|---|---|---|---|---|---|---|
| orig frac 5* | 7 | 41 | 92 | 0 | −9 | 0 |
| orig 10* | 75 | 81 | 97 | 6 | 0 | 6 |
| orig 11* | 25 | 26 | 82 | 0 | −8 | 0 |
| orig HOAc* | 0 | −14 | 57 | 0 | −15 | 16 |
| 1-11 (frac3) | 37 | 85 | 99 | 0 | 10 | 12 |
| 1-11 (frac7) | 81 | 89 | 99 | 9 | 12 | 11 |
| 1-11(frac14-17) | 69 | 68 | 87 | | | |
| 1-11 (frac10) | 96 | 97 | 100 | | | |
| acids 3-7 E | 89 | 81 | 98 | | | |
| acids 8-14 F | 7 | −15 | 7 | 0 | | |
| HS804/119/1 | 0 | −21 | 26 | −18 | | |
| HS804/120/1 | −10 | 0 | 26 | −11 | | |
| HS804/120/2 | −13 | 0 | 81 | 0 | 0 | 10 |
| HS804/120/3 | 26 | 30 | 54 | 13 | −12 | 66 |
| HS804/120/5 | −21 | −61 | 35 | 13 | | |
| HS804/122/5 | 0 | 6 | 30 | −8 | | |
| HS804/122/8 | 0 | −8 | 92 | 0 | −9 | 29 |
| HS804/122/10 | 0 | 0 | 90 | 0 | | |
| HS804/122/18 | 0 | −11 | 98 | 19 | 0 | 62 |
| sucrose 10 mg/ml | 0 | −7 | 0 | 0 | 0 | 0 |

TABLE 9-continued

Activity (% inhibition) of Sugar Fractions on Glycosidases

| sample | α-D-mannosidase (Jack bean) | naringinase (P. decumbens) | N-acetyl-β-D-gluc (Bovine kidney) | N-acetyl-β-D-gluc (Jack bean) | amyloglucosidase (A. niger) | β-glucuronidase (bovine liver) |
|---|---|---|---|---|---|---|
| orig frac 5* | | −7 | 0 | 0 | 0 | −7 |
| orig 10* | | 0 | 9 | 7 | 24 | 0 |
| orig 11* | | 0 | 0 | 0 | 6 | 0 |
| orig HOAc* | | −6 | 0 | 0 | 0 | 0 |
| 1-11 (frac3) | 0 | | | 0 | | |
| 1-11 (frac7) | 0 | | | 11 | | |
| 1-11 (frac14-17) | | | | | | |
| 1-11 (frac10) | | | | | | |
| acids 3-7 E | | | | | | |
| acids 8-14 F | | | | | | |
| HS804/119/1 | | | | | | |
| HS804/120/1 | | | | | | |
| HS804/120/2 | 0 | | | −12 | | |
| HS804/120/3 | 0 | | | −16 | | |
| HS804/120/5 | | | | | | |
| HS804/122/5 | | | | 0 | | |
| HS804/122/8 | 0 | | | 0 | | |
| HS804/122/10 | | | | | | |
| HS804/122/18 | 8 | | | −37 | | |
| sucrose 10 mg/ml | | | 0 | 0 | | |

Substrates are 10 mM p-nitrophenyl-glycopyranosides.
Enzymes are purchased from Sigma and run at the pH optima Substrates are 10 mM p-nitrophenyl-glycopyranosides. Enzymes are purchased from Sigma and run at the pH optima The CG400 OH— retained material samples (C and D) were further fractionated using CG400 in the acetate form.

Sample C (HS0804/119) gave a good separation as did sample D (HS0804/120)

The compounds in C resembled mono and disaccharide sugars but the common sugars would not be retained on CG400.

Sample D showed some similar compounds but also some larger molecules around 24-25 minute retention times.

The amount and activity of fractions C and D are set out in the tables below:

TABLE 10

Weights of fractions from acid sample C fractionated on CG400 acetate form

| Fraction | Weight mg | Notes |
|---|---|---|
| HS0804/119/1 | 437 | Assays |
| 119/2 | 31 | |
| 119/3 | 4.4 | |
| 119/4 | 2 | |
| 119/5 | 9.9 | |

TABLE 11

Weights of fractions from acid sample D fractionated on CG400 acetate form

| Fraction | Weight mg | Notes |
|---|---|---|
| HS0804/120/1 | 125 | Assays |
| 120/2 | 643 | Assays |
| 120/3 | 11.4 | Assays |

TABLE 11-continued

Weights of fractions from acid sample D fractionated on CG400 acetate form

| Fraction | Weight mg | Notes |
|---|---|---|
| 120/4 | 6.5 | |
| 120/5 | 76.2 | Assays |

The samples C and D fractionated well on the acetate columns.

Sample HS120/2 was further fractionated on a 2×10 cm column of CG400 acetate form resin using 5 ml water fractions followed by 1M HOAc to give samples HS0804/122

TABLE 12

Weights of Fractions from HS0804/120/2

| Fraction | Weight mg | notes |
|---|---|---|
| HS0804/122/1-3 | 0 | |
| 122/4 | 204 | |
| 122/5 | 189 | assays |
| 122/6 | 141 | |
| 122/7 | 55 | |
| 122/8 | 22 | assays |
| 122/9 | 15 | |
| 122/10 | 15 | assays |
| 122/11 | 8 | |
| 122/12 | 3.4 | |
| 122/12-17 | 19 | |
| 122/18 HOAc | 11.9 | assays |

GC-MS analysis of these samples revealed a good separation and several components of interest.

Fractions 5, 8, 10 and 18 were submitted for assays.

These samples showed an interesting selectivity for the rice glucosidase which was also evident in the first HOAc samples produced in Example 2

The fractions from samples 1-11 tended to give good inhibition of not only the rice glucosidase but also the yeast and *bacillus* enzyme.

GC-MS analysis of the HS0804/122 fractions showed several potentially novel components. One component in the 122/18 gave a mass spectrum fairly typical of an imino-sugar and some other compounds had some similarities in fragmentation to imino-sugars.

Discussion and Conclusions

From the 10 g PhynoRadiance sample was obtained 5.026 g of a sugar fraction. After anion exchange chromatography this reduced to 3.728 g by possible removal of inorganic or aromatic material. This fraction comprising 37% of the PhynoRadiance sample had significant glycogen phosphorylase inhibition activity and also potently inhibited three alpha-glucosidases. This Example has confirmed the activity of the sugars of PhynoRadiance and determined that there are some larger sugars with activity and some possible sugar acids (imino-sugar acids) giving inhibition more selectively to a rice alpha-glucosidase.

Selectivity of activity amongst glucosidases has been shown to be important for treating some disorders because there are many glucosidases active in mammalian systems and blanket inhibition of all glucosidases can cause some off-target effects. It should also be noted that inhibitors of glucosidases can also have beneficial effects on cells producing deficient glycoproteins by chaperoning activity; such effects could be surmised to be related to anti-ageing properties (Best et al., 2010)

The glycosidase assays of the original sugar fractions from Example 2 were extended and show that the Phyno-Radiance sugar fraction shows particularly good inhibition of a range of alpha-glucosidases but an extensive set of other glycosidases has not been run. This inhibition profile is somewhat similar to that of DNJ except that DNJ does not also inhibit glycogen phosphorylase. The sugar fractionation and assays tends to show that the retained components inhibit particularly the rice glucosidase whereas the un-retained components inhibit all three alpha-glucosidases tested. Glycogen phosphorylase inhibition was found in both CG400 OH— retained and un-retained fractions.

GC-MS analysis of the CG400 OH— unretained fractions from sample 1-11 was not very informative but NMR revealed quite pure looking sugars presumed to be larger than disaccharides. The CG400 retained components gave good GC-MS data and appear quite complex; some disaccharides are present (not sucrose) but also unusual sugars or imino-sugars (presumably with carboxyl-groups or aromatic units to have retained on CG400 initially). It was concluded that the sugar fraction contains some novel sugars with potent glycosidase and glycogen phosphorylase activity. The likelihood is that the larger sugars seen in the un-retained CG400 OH— fractions are novel and have imino-sugars conjugated to them giving activity. The retained compounds on CG400 OH— may be smaller units that are being released from the larger sugars or are novel sugar acids.

The NMR data collected for sample A (a highly active un-retained CG400OH-fraction from sample 1-11) showed good purity but very little structural information is obtained on such larger sugars.

Example 4

Example 4 sought to confirm the activity in non-imino-sugar fractions of the extracts.

SUMMARY

This Example confirmed that N-acids of DNJ and DAB present in a mulberry extract give more selective inhibition of alpha-glucosidases than DAB and DNJ and these compounds also give good inhibition of mammalian β-glucuronidase, hexosaminidase and α-L-iduronidase.

Serum β-glucuronidase and hexosaminidases are elevated in several diseases including diabetes.

Elevation of β-glucuronidase could result in poor excretion of toxins as glucuronides and hence inhibition of this enzyme could be beneficial to health It is reported that imino sugars can act as both inhibitors and chaperoning molecules for glycosidases and hence may also increase the activity of glycosidases they inhibit at sub-inhibitory concentrations.

The N-acids of DNJ and DAB are novel isolated natural products.

An unusual trisaccharide, with a deoxy-sugar and an aryl-glycoside has also been tentatively identified.

Material Studied

IminoNorm 200 ml crude extract; and

PhynoRadiance 50 g batch as set out in Table 13.

TABLE 13

| Sample | IR120 retained Weight in g | IR120 unretained weight in g |
|---|---|---|
| IminoNorm | 54.64 (too viscous to dry fully) | 28 |
| PhynoRadiance | 1.38 | 32 |

Analysis

GC-MS

This was as per Example 1.

NMR

This was as per Example 1.

Glycosidase Assays

This was as per Example 1.

Methods of Purification

The further fractionation of the sugar samples involved use of the strongly basic anion exchange resin CG400 in the OH— form and the acetate form.

Fractions were collected in water and freeze dried as described in Example 3

Retained material was removed using 1M acetic acid and these fractions were evaporated nearly to dryness by rotary evaporation and then freeze dried.

Results

Table 14 below provides α-Glycosidase results (% inhibition at 2 mg/ml) for IminoNorm and PhynoRadiance Anion Exchange Resin (CG400) un-retained and retained Fractions.

|  | (Yeast) | (Bacillus) | (rice) |
|---|---|---|---|
| IminoNorm unretained | 85 | 99 | 100 |
| PhynoRadiance unretained | 33 | 88 | 99 |
| PhynoRadiance retained | 0 | 12 | 96 |
| IminoNorm retained HOAc | 6 | 24 | 97 |

The samples IminoNorm and PhynoRadiance (diluted extracts as described in WO2011/032502) were additionally subjected to:
1) Cation exchange chromatography; and
2) Anion exchange chromatography, as described in the previous examples.

The anion exchange retained material gave a more specific inhibition of rice α-glucosidase.

The anion exchange resin un-retained material, of both samples, gave broader α-glucosidase inhibition.

The N-acids of the imino sugars DAB and DNJ appear to be responsible for the specific rice α-glucosidase inhibition (See glycosidase Table 16).

There was proportionally more weight of material retained by the anion exchange resin (Table 15) from IminoNorm (71%) probably due to its greater dilution with sugars.

Sugars added to PhynoRadiance may have, therefore, contributed to the weight of anion exchange un-retained fractions of that sample.

Both samples had inhibitory activity, however, and so the added sugars of PhynoRadiance do not necessarily have the activity which seems to come from mulberry itself.

TABLE 15

| Sample | % retained on anion exchange resin but displaced by HOAc | % not retained on anion exchange resin | % weight not retrieved from anion exchange resin |
|---|---|---|---|
| IminoNorm (diluted to 2% DNJ) | 71 | 29 | 38 |
| PhynoRadiance (diluted to 5% DNJ) | 56 | 44 | 20.5 |

DNJ was the major component of both pre-fractionated extracts.

GC-MS Chromatograms (and mass spectrum) are provided in FIGS. 1-13

Figure 1:
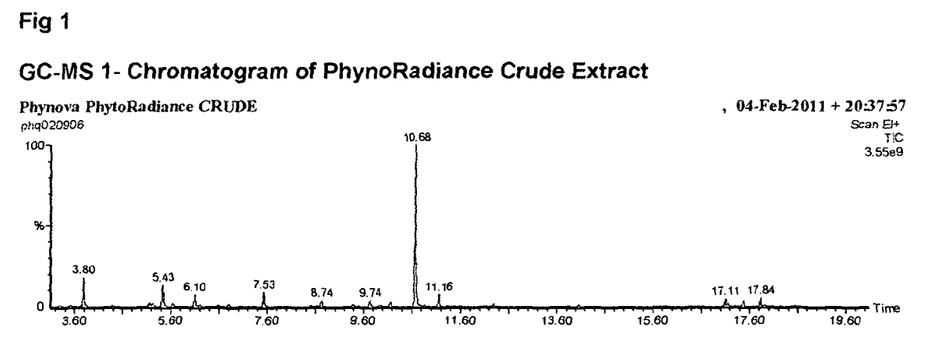
FIG. 1 is a GC MS chromatogram of PhynoRadiance crude extract.
Figure 2:
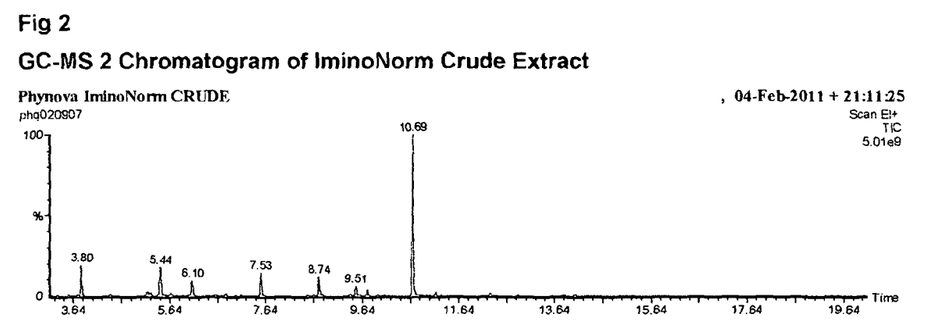
FIG. 2 is GC-MS Chromatogram of IminoNorm crude extract.
Figure 3:
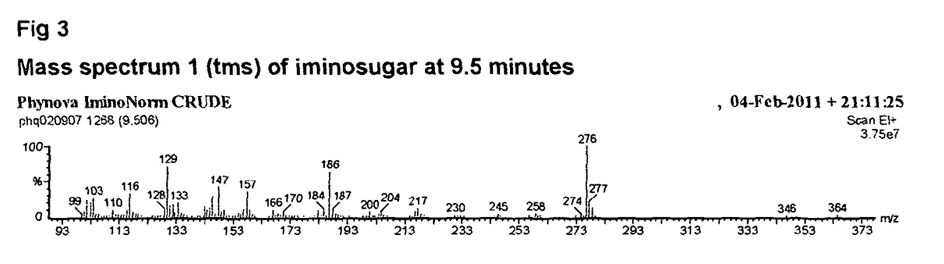
FIG. 3 is a Mass spectra (tms) of iminosugar at 9.5 minutes.

Referring to these Figs the following is noted:

FIGS. 1 and 2 are GC-MS Chromatograms of PhynoRadiance and IminoNorm Crude Extracts. It will be noted that in the IminoNorm Chromatogram some imino sugars appear in relatively higher concentrations. One is the compound having a mass spectrum as shown in FIG. 3 (9.5 minute).

Figure 4:
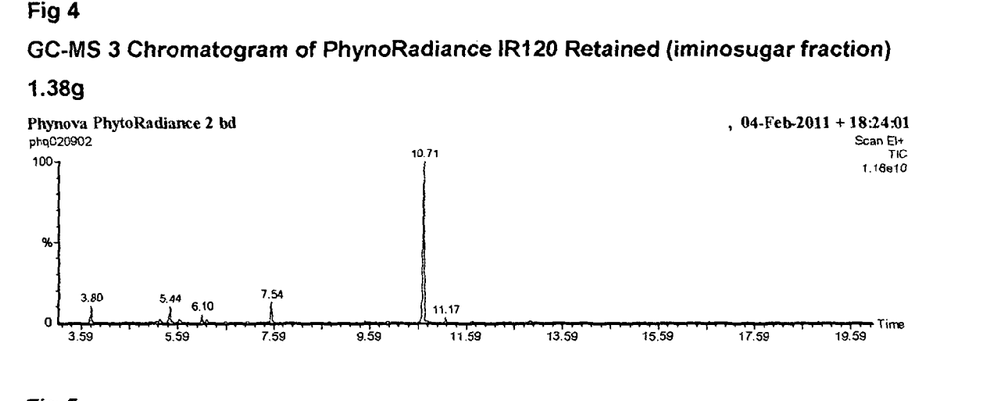
FIG. 4 is a GC-MS Chromatogram of PhynoRadiance IR120 Retained (iminosugar fraction) 1.38 g.
Figure 5:
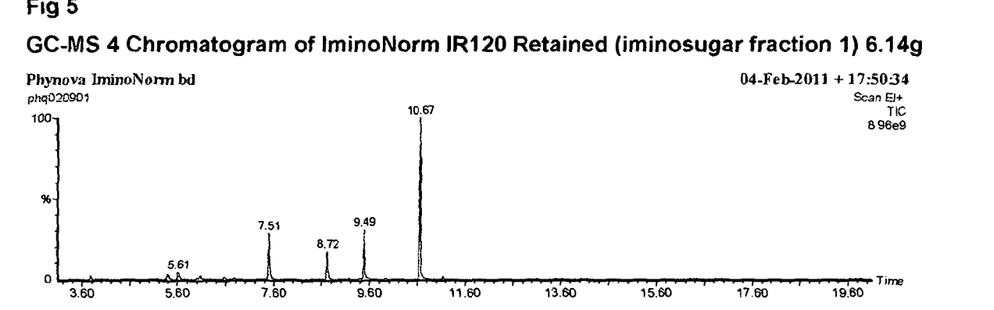
FIG. 5 is a GC-MS Chromatogram of IminoNorm IR120 Retained (iminosugar fraction 1) 6.14 g.

FIGS. 4 and 5 are GC-MS Chromatogram of PhynoRadiance IR120 Retained (iminosugar fraction) 1.38 g and IminoNorm IR120 Retained (iminosugar fraction 1) 6.14 g respectively.

The iminoNorm sample overloaded the cation exchange resin (IR120) two times due to the high imino sugar content.

Figure 7A:
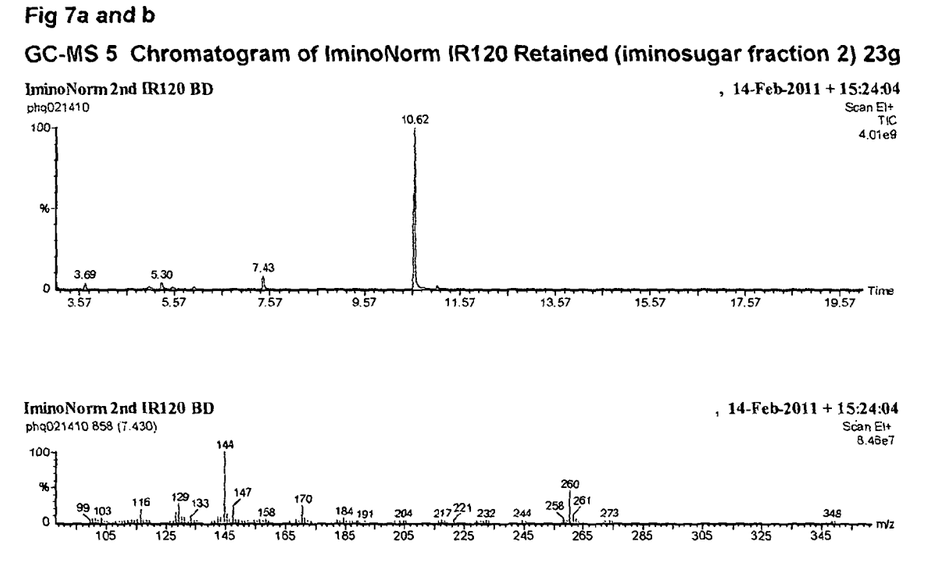
FIGS. 7a and b are a GC-MS Chromatogram of IminoNorm IR120 Retained (iminosugar fraction 2) 23 g and a Mass spectra for Fagomine.
Figure 8A:
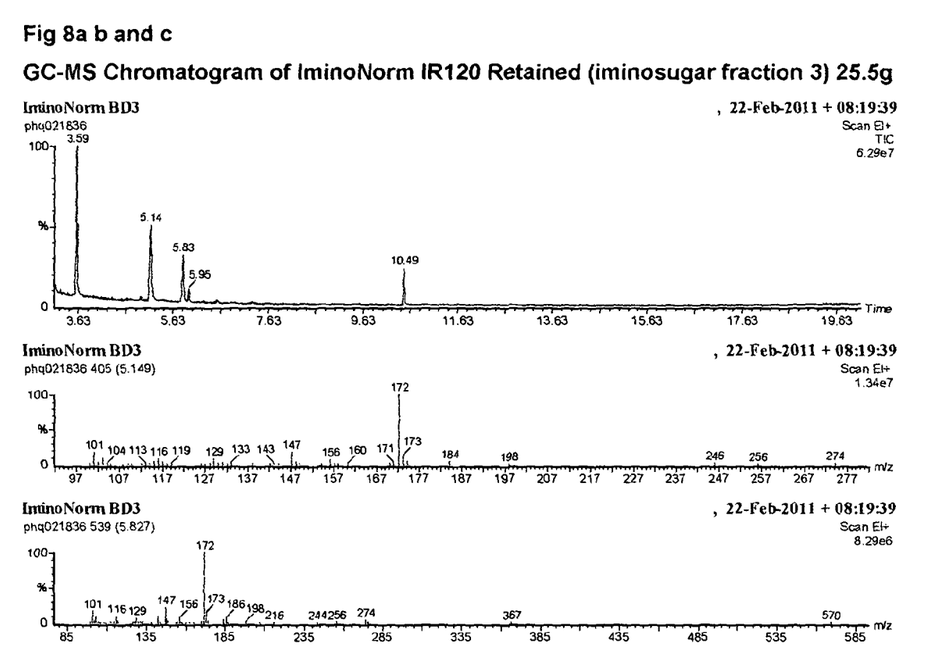
FIGS. 8a, b and c are a GC-MS Chromatogram of IminoNorm IR120 Retained (iminosugar fraction 3) 25.5 g and two Mass spectra of hydroxylated pipecolic acids.

Bound fractions (2 and 3) are shown in FIGS. 7 and 8 with some preferential displacement of imino sugars evident. Basic imino sugars tend to displace more neutral or acidic imino sugars.

Two related imino sugars only just visible in PhynoRadiance are quite major in the IminoNorm IR120 bound fraction 1 and this could be used to purify and identify those iminosugars (8.72 and 9.49 minutes).

The selective displacement also allowed the further characterisation of three N-acids of DAB and DNJ which are new natural products. These N-acids also occur in PhynoRadiance.

Figure 6A:
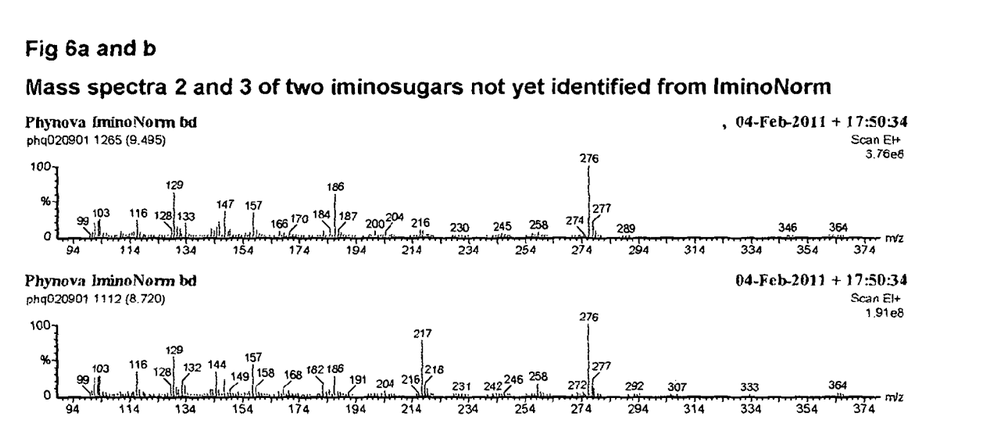
FIGS. 6a and b are the Mass spectra of two iminosugars not yet identified from IminoNorm.

FIGS. 6a and b are the Mass spectra of two iminosugars not yet identified from IminoNorm.

FIG. 7a is a GC-MS Chromatogram of IminoNorm IR120 Retained (iminosugar fraction 2) 23 g and FIG. 7b is a Mass spec for Fagomine.

DNJ is by far the major imino sugar in the $2^{nd}$ IminoNorm retained fraction on IR120. The iminosugar at 7.4 minutes is fagomine.

FIG. 8a, is a GC-MS Chromatogram of IminoNorm IR120 Retained (iminosugar fraction 3) 25.5 g. FIGS. 8B and 8C are two Mass spec of hydroxyllated pipecolic acids.

Hydroxylated pipecolic acids are more major than DNJ in the $3^{rd}$ IR120 retained fraction of IminoNorm. Their mass spectra and one identified in Example 2 are shown below. The major component at 3.59 minutes could be phenylalanine.

Figure 9:
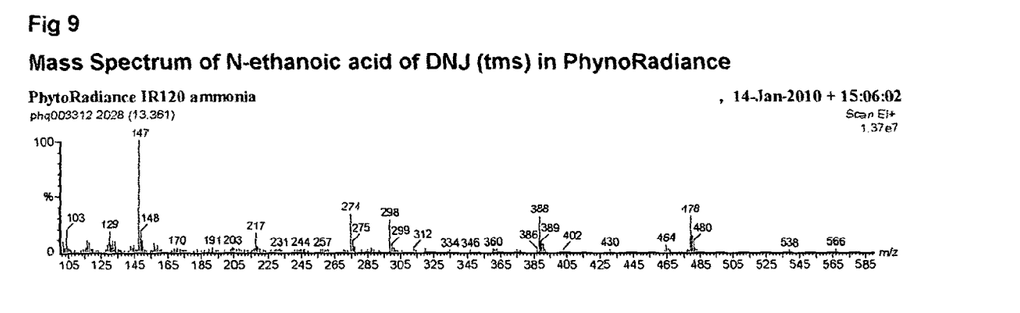
FIG. 9 is a Mass Spectra of N-ethanoic acid of DNJ (tms) from PhynoRadiance

FIG. 9 is a Mass Spectra of N-ethanoic acid of DNJ (tms) in PhynoRadiance.

Figure 10:
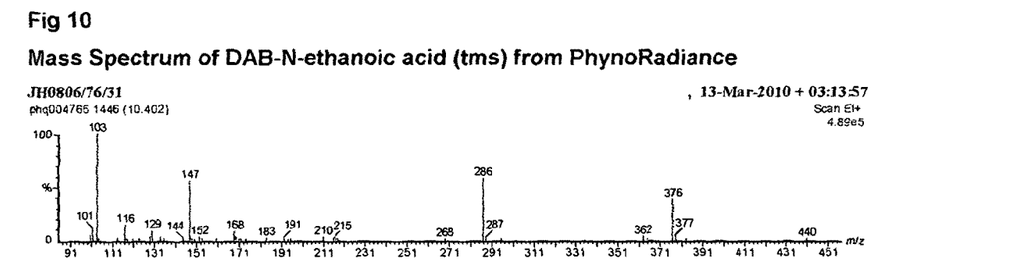
FIG. 10 is a Mass Spectra of DAB-N-ethanoic acid (tms) from PhynoRadiance

FIG. 10 is a Mass Spectra of DAB-N-ethanoic acid (tms) from PhynoRadiance.

Figure 11:
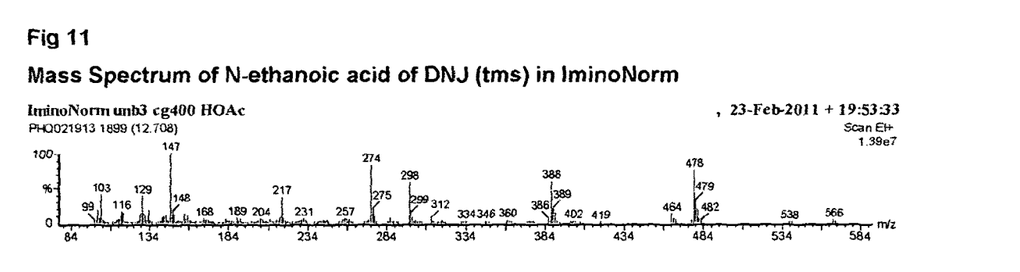
FIG. 11 is a Mass Spectra of N-ethanoic acid of DNJ (tms) from IminoNorm

FIG. 11 is a Mass Spectra of N-ethanoic acid of DNJ (tms) in IminoNorm.

Figure 12:
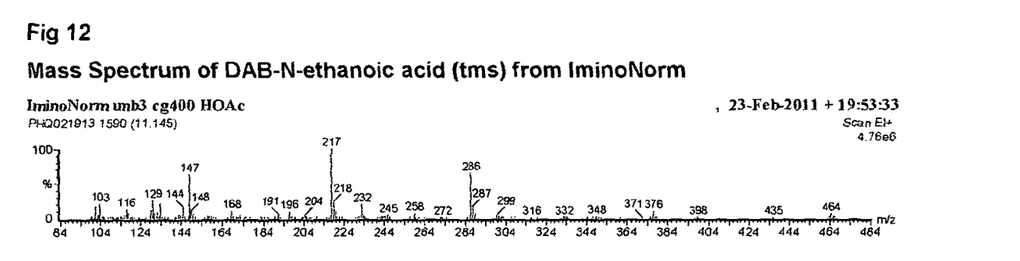
FIG. 12 is a Mass Spectra of DAB-N-ethanoic acid (tms) from IminoNorm.

FIG. 12 is a Mass Spectra of DAB-N-ethanoic acid (tms) from IminoNorm; and

Figure 13:
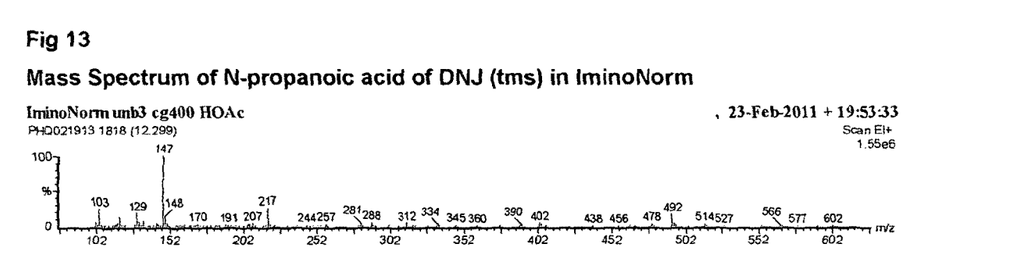
FIG. 13 is Mass Spectra of N-propanoic acid of DNJ (tms) from IminoNorm.

FIG. 13 is Mass Spectra of N-propanoic acid of DNJ (tms) in IminoNorm.

The formula for these acids are illustrated in Formula 8 to 10 below:

Formula 8

N-ethanoic acid of DAB

Formula 9

N-ethanoic acid of DNJ

Formula 10

N-propanoic acid of DNJ

The N-acids of DAB and DNJ are visible in the Phyno Radiance extract without concentration but are less obvious in IminoNorm. They are, however, present in both samples.

The activity of these novel isolated acids is shown in Table 16 below.

| Assay | DNJ | DAB | DAB-N-ethanoic | DNJ-N-propanoic | DNJ-N-ethanoic |
|---|---|---|---|---|---|
| α-D-glucosidase (Yeast) | 36 | 100 | 10.7 | 0.0 | 2.5 |
| α-D-glucosidase (Bacillus) | 100 | 93 | 24.2 | 45.0 | 9.1 |
| α-D-glucosidase (Rice) | 100 | 100 | 42 | 100 | 100 |
| β-D-glucosidase (yeast) | 64 | 100 | 7 | 32 | 14 |
| α-D-galactosidase (Green coffee beans) | −3 | 7 | −5 | 15 | −8 |
| β-D-galactosidase (Bovine) | 0 | 100 | 0 | 12 | 2 |
| α-L-fucosidase (Bovine) | 6 | 5 | 3 | 11 | 5 |
| α-D-mannosidase (Jack bean) | 27 | 3 | 28 | 40 | 38 |
| β-D-mannosidase (C. fimi) | −19 | 95 | −5 | −5 | −10 |
| Naringinase (P. decumbens) | 21 | 3 | 0 | 4 | 0 |
| N-acetyl-β-D-gluc (Bovine kidney) | 0 | −8 | 82 | 86 | 84 |
| Amyloglucosidase | 32 | 47 | −2 | 53 | 0 |

DNJ-N-propanoic acid has an $IC_{50}$ against bovine liver β-glucuronidase of 340 uM and 383 uM on human recombinant α-L-iduronidase.

DAB-N-ethanoic acid has an $IC_{50}$ against β-glucuronidase of 523 uM and 196 uM on the iduronidase.

DNJ-ethanoic acid has an $IC_{50}$ on bovine β-glucuronidase of 208 uM but only weakly inhibits the iduronidase at 0.8 mM.

Discussion and Conclusions

Example 4 demonstrates that once DNJ is removed there is great similarity in the glycosidase inhibition profiles of PhynoRadiance and IminoNorm.

There are N-acids of DNJ and DAB in both samples which give more selective inhibition of α-glucosidases than DAB and DNJ but these compounds also give good inhibition of mammalian β-glucuronidase, hexosaminidase and α-L-iduronidase.

Selective fractions containing these compounds have clear application as pharmaceuticals and food ingredients.

Serum β-glucuronidase and hexosaminidases are elevated in several diseases including diabetes and Alzheimer's. Elevation of β-glucuronidase could result in poor excretion of toxins as glucuronides and hence inhibition of this enzyme could be beneficial to health. It is reported that iminosugars can act as both inhibitors and chaperoning molecules for glycosidases and hence may also increase the activity of glycosidases they inhibit at sub-inhibitory concentrations.

The N-acids of DNJ and DAB are novel natural products.

One can conclude from the Examples that there are several compounds contributing to glycosidase inhibitions in both PhynoRadiance and IminoNorm. These include DNJ, DAB, fagomine, hydroxylated pipecolic acids, N-acids of DAB and DNJ and other, as yet, not characterised iminosugars. An aryl-glycoside and sugars including a trisaccharide may also be giving inhibition of glycosidases and glycogen phosphorylase.

Thus selective water soluble Morus extracts rich in hydroxylated pipecolic acids, N-acids of DAB and DNJ and which contain significantly reduced levels of the imino acids DNJ, DAB and Fagomine or substantially pure hydroxylated pipecolic acids, N-acids of DAB and DNJ can be used in medicine. The acids include N-ethanoic DAB and N-ethanoic DNJ.

Example 5

Methodology:

The efficacy of an extract of the invention (PYN 8) to reduce post-prandial blood glucose spikes was evaluated in an acute sugar challenge ddy mouse model. Ten mice were divided into two groups, the treatment groups and placebo group. Animals orally received 2.5 g/kg body weight maltose, with either 500 mg/kg PYN8 (active arm) or saline (control). Blood glucose concentration was measured at time points 0, 15 min, 30 min, 60 min and 120 min to evaluate any effects on reduction of blood glucose following the ingestion of maltose.

Figure 14:
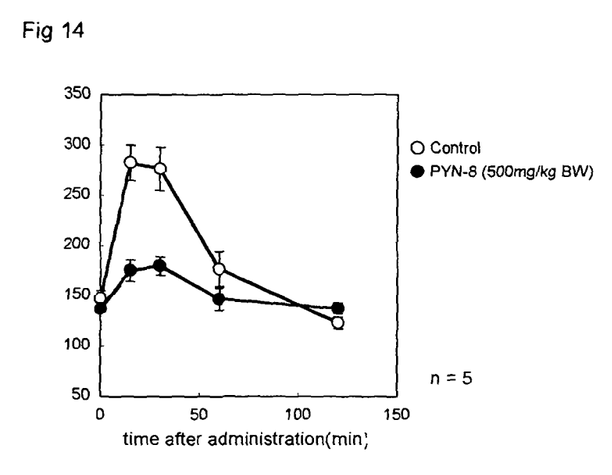
FIG. 14 is a graph showing the effect of an extract of the invention on blood glucose levels in mice.

Results:

The extract of the invention was shown to significantly reduce blood glucose levels after a maltose challenge as illustrated in FIG. 14.

Conclusions:

The in vivo study confirmed the in vitro findings that the extract of the invention could significantly reduce post-prandial blood glucose levels. The extract inhibits multiple glucosidase enzymes that are involved in glucose metabolism. The in vivo study shows that the extract is bioavailable and is not inactivated by stomach acid, stomach enzymes or by an active metabolism.

The invention claimed is:

1. A purified extract comprising greater than 5% (w/w) of N-acids of imino sugars and pipecolic acids by weight of the extract, wherein the extract is obtainable from mulberry leaf, is water soluble, and inhibits α glucosidase;
   wherein at least one of:
   the N-acids of imino sugars comprise by weight 5-25% of the extract; and
   the pipecolic acids comprise by weight 5-35% of the extract;
   wherein the N-acids of imino sugars comprise C1-C9 alkyloic acids of DAB, DNJ, fagomine, and calystegine B2;
   wherein the imino sugars comprise greater than 0% and not more than 19% (w/w) DNJ of the imino sugar content;
   wherein the extract further inhibits glycogen phosphorylase; and wherein the extract selectively inhibits rice α-glucosidase.

2. The purified extract of claim 1, wherein the at least one of N-acids of imino sugars and pipecolic acids comprise at least 10% of the extract.

3. The purified extract of claim 1, wherein the C1-C9 alkyloic acids include at least one of ethanoic acid, propanoic acid, and butanoic acid.

4. The purified extract of claim 1, further comprising oligosaccharides and amino acids.

5. The purified extract of claim 4, further having a mass balance in which at least one of:
   oligosaccharides comprise by weight 5-25% of the extract; and
   amino acids comprise by weight 25-75% of the extract.

6. The purified extract of claim 5, wherein the amino acids comprise acidic amino acids.

7. The purified extract of claim 1, wherein the extract is a semi crystalline material.

8. The purified extract of claim 1, further having a purified weight of at least a factor 200 compared to a weight of the starting material.

9. The purified extract of claim 1, wherein the extract further acts as at least one of a naringinase inhibitor, a glucosidase inhibitor, a mannosidase inhibitor, a glucuronidase inhibitor, a hexosaminidase inhibitor, an α and β galactosidase inhibitor, or an l-d-uronidase inhibitor.

10. The purified extract of claim 1, wherein the extract is obtained from at least one of *Morus alba* L, *Morus alba* var. *multicaulis* L, *Morus nigra*, and *Morus australis* Poir.

11. The purified extract of claim 1, wherein the extract is obtained using a strongly acidic cation exchange resin and at least one of a strongly basic anion exchange resin and a weakly basic anion exchange resin in the purification process.

12. A pharmaceutical preparation, dietary supplement, and a food ingredient comprising a purified extract having greater than 5% (w/w) of N-acids of imino sugars and pipecolic acids by weight of the extract, wherein the extract is obtainable from mulberry leaf, is water soluble, and inhibits α glucosidase;
   wherein at least one of:
      the N-acids of imino sugars comprise by weight 5-25% of the extract; and
      the pipecolic acids comprise by weight 5-35% of the extract;
   wherein the N-acids of imino sugars comprise C1-C9 alkyloic acids of DAB, DNJ, fagomine, and calystegine B2;
   wherein the imino sugars comprise greater than 0% and not more than 19% (w/w) DNJ of the imino sugar content;
   wherein the extract further inhibits glycogen phosphorylase; and
   wherein the extract selectively inhibits rice α-glucosidase.

13. The purified extract of claim 1, wherein the extract is used for treatment of metabolic disorders including diabetes.

14. The purified extract of claim 1, wherein the extract provides at least one of reduced post-prandial blood glucose levels, reduced gluconeogenesis, reduced insulin resistance, weight loss, blood lipid management, and beta cell protection and restoration.

15. The purified extract of claim 1, wherein the imino sugars comprise greater than 0% and not more than 5% (w/w) DNJ of the imino sugar content.

16. The purified extract of claim 1, further having a purified weight of at least a factor 1000 compared to a weight of the starting material.

* * * * *